United States Patent [19]

Loiterman

[11] 4,017,193
[45] Apr. 12, 1977

[54] APPARATUS FOR MEASURING THE TRANSMITTANCE OR OPACITY OF A GASEOUS MEDIUM CARRYING PARTICULATE MATTER THROUGH A CONDUIT

[76] Inventor: Leo Loiterman, c/o American Electric Power Service Corp., 2 Broadway, New York, N.Y. 10004

[22] Filed: Mar. 2, 1976

[21] Appl. No.: 663,090

[52] U.S. Cl. .............................. 356/206; 250/575; 340/237 S; 356/207
[51] Int. Cl.² ....................................... G01N 21/26
[58] Field of Search ............ 356/206, 207; 250/575

[56] References Cited

UNITED STATES PATENTS

| 3,652,850 | 3/1972 | Briggs | 356/206 |
| 3,973,852 | 8/1976 | Moore et al. | 356/207 |
| 3,976,891 | 8/1976 | Parkinson | 356/207 |

*Primary Examiner*—John K. Corbin
*Assistant Examiner*—R. A. Rosenberger
*Attorney, Agent, or Firm*—Pennie & Edmonds

[57] ABSTRACT

The apparatus has spaced light sources and light sensors on opposite walls of a conduit positioned to provide a pair of equal shorter path lengths and a pair of equal longer path lengths for narrow collimated beams between the sources and sensors. Each sensor is exposed to beams from the sources alternately during measuring periods. Computing means computes the quotient of the products of the sensor outputs corresponding to light transmitted over the longer and shorter paths, and an output is produced from the quotient corresponding to the transmittance or opacity over a predetermined distance of smoke, etc. Test means are provided to monitor the operation continually. Beam splitters for the sources, and disks having transparent and mirror sectors for the sensors, are described. Mirror sectors of different reflectivity operate during measuring and test periods. Windows are employed at the sources and sensors and the apparatus largely compensates for dirt build-up on the windows, and variations in the sources and sensors. Specific features to promote accuracy are described.

19 Claims, 14 Drawing Figures

APPARATUS FOR MEASURING THE TRANSMITTANCE OR OPACITY OF A GASEOUS MEDIUM CARRYING PARTICULATE MATTER THROUGH A CONDUIT

This invention relates to the measurement of the transmittance or opacity of a gaseous medium carrying particulate matter, smoke for example, in a conduit.

At the present time environmental protection dictates that the particulate content of stack emissions for power plants and similar installations be limited to acceptable levels. This requires continuous monitoring and frequaent checking of the preformance of the monitoring apparatus.

Measuring optical transmittance or opacity of the smoke, etc. is one of the means available to evaluate the amount of particulate matter being discharged to the atmosphere. Since the amount will depend on the dimensions of the smoke stack, etc. as well as on the density of the particles in the gas, in general it is desired to determine that transmittance or opacity over a predetermined distance such as the stack diameter so that appropriate standards can be established and ccompliance therewith can be determined.

To determine light transmittance or opacity it is necessary to transmit light through the gaseous medium and measure variations in attenuation produced by the particles therein. Variations in the intensity of the light source and in the sensitivity of the light sensor will commonly affect the measurement. Also accumulation of dirt on optical windows through which the light passes will affect the measurement. In addition, scattering of the transmitted light by smoke particles and the like in the gaseous medium may affect the measuring accuracy.

The present invention provides apparatus in which the measuring accuracy is substantially unaffected by variations in light source brightness and photosensor sensitivity, or by scattered light, and in which unequal dirt build-up on optical windows is largely compensated. In addition, test means are provided which permits checking the operation of the apparatus at frequent intervals, and preferably in test periods which alternate with measuring periods.

To this end the apparatus comprises spaced first and second light sources and spaced first and second light sensors positioned on opposite walls of a conduit through which the smoks, etc. passes. The sources and sensors are positioned to provide equal shorter path lengths between first source and first sensor and between second source and second sensor, and equal longer path lengths between first source and second sensor and between second source and first sensor. Advantageously the first and second sensors are directly across the conduit from the first and second sources respectively, and the second and first sensors are diagonally across the conduit from the first and second sources respectively, and preferably the diagonal light paths make angles of approximately 45° with respect to the direct light paths.

Means are provided at each light source for producing and directing narrow collimated beams toward each light sensor, and at each light sensor for producing narrow reception beam angle. Means are also provided for exposing each sensor to beam from the sources alternately during measuring periods, and directing the beams to the sensor at the reception beam angle thereof. A particular advantage of this arrangement is the avoidance of errors due to scattering of light rays by the particles in the gaseous medium. Advantageously collimating and beam splitting means are located between each light source and its window, and a rotating disk and collimating means are located between each sensor and its window. The disk has transparent and mirror sectors for directing light from the two sources alternately to the corresponding sensor.

The output signals of the sensors are fed to computing means which produces the quotient of the products of the output corresponding to light transmitted over the longer and over the shorter paths. As will be shown hereinafter, the quotient is proportional to the square of the transmittance of the smoke, etc. over a distance equal to the difference between the longer and shorter path lengths, and is independent of the brightness of the sources and the sensitivity of the sensors. Also, with proper placement of the sources and sensors, preferably in a plane parallel or perpendicular to the paht of travel of the smoke, etc. in the conduit, the quotient is largely independent of dirt build-up on the windows between the sources and sensors and the conduit. The computing means produces from the quotient an output corresponding to the transmittance ro opacity or a predetermined distance of the smoke, etc. The predetermined distance can be, for example, the stack exit diameter of a power plant.

Advantageously the sensors simultaneously receive light from one source transmitted over respective shorter and longer path lengths, and alternately receive light from the other source transmitted over respective longer and shorter path lengths. The computer means may then produce ratios of the sensor outputs corresponding to light transmitted thereto over the shorter and longer path lenghts, and vice versa, and the ratios used to produce the quotient.

Preferably the apparatus includes test means which provides a continual check on the measuring accuracy. To this end, test means are provided adjacent each sensor for reducing the light transmitted to the sensor over one of the path lenghts by a predetermined fraction during test periods alternating with the measuring periiods. The computing means produces the aforesaid quotient from the sensor outputs produced during the test periods, the relationship of this quotient to the quotient produced during a measuring period being determined by the aforesaid fraction of light reduction. Accordingly the quotients corresponding to the measuring and test periods may be used to produce test signal outputs which will indicate departures from proper operation.

In the specific embodiment described hereinafter, test signal components ae produced from the quotients corresponding to the measuring and test periods, one of the components is multiplied by a factor compensating for the predetermined ratio of light supplied to thesensors during measuring and test periods over one of the paths, and the compensated component compared with the other component to yield a test signal output.

With revolving disks at the sensors, as described above, mirror sectors of high and lower reflectivity may be used to reflect light to the corresponding sensor which is of full intensity during measuring periods and a fraction of full intensity, say half intensity, during test periods. The aforesaid compensating factor for one of the test signal components is then determined by the difference in reflectivity of the mirrors.

DETAILED DESCRIPTION OF THE SPECIFIC EMBODIMENTS

Figure 1:
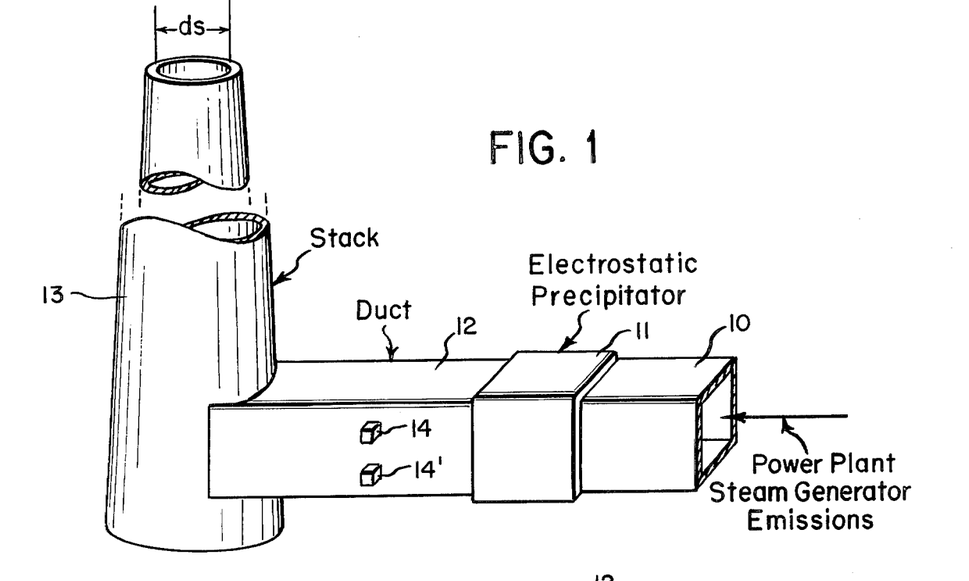
FIG. 1 is an overall view illustrating the use of the invention for mointoring emissions from a power plant.

Reffering to FIG. 1, an example of a particular environment in which the invention may be used is given. Emissions from a fossil fueled power plant in conduit 10 pass through an electrostatic precipitator 11 and a duct 12 to a stack 13. The duct has a rectangular cross-section. The gaseous medium in the duct carries particulate matter, not removed by the precipitator, which is discharged from the stack to the atmosphere. In this example duct 12 is the conduit used for measuring purposes and smoke flows therethrough.

Figure 2A:
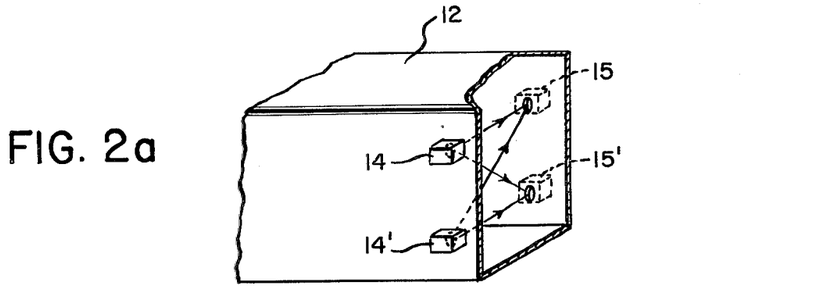
FIGS. 2a–2c illustrate various arrangements of the light sources and light sensors in accordance with the invention.
Figure 2B:
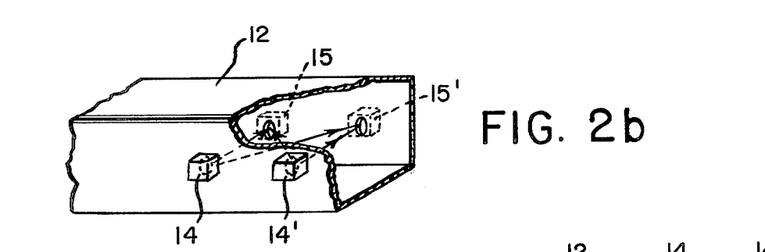
Figure 2C:
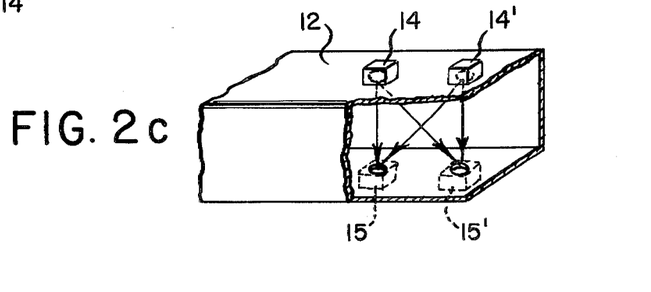

In FIG. 2a a pair of spaced light sources 14, 14' are positioned on one side wall of the duct 12, and a pair of spaced light sensors 15, 15' are positioned on the opposite side wall. The sources and sensors are in a plane which is perpendicular to the axis of the duct. In FIG. 2b the sources and sensors are positioned on opposite side walls in a plane parallel to the emission flow. The arrangement of FIG. 2c is similar to 2b, but the sources and sensors are on the top and bottom walls of the duct.

Figure 3:
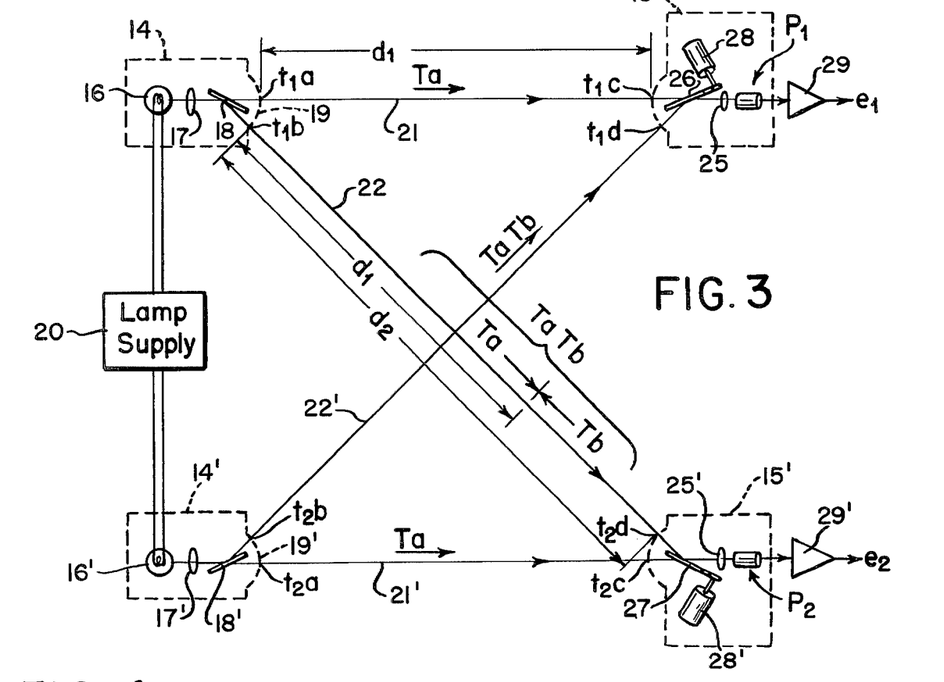
FIG. 3 is an explanatory diagram showing the optical paths between the light sources and light sensors of FIG. 2.

Referring to FIG. 3, the light sources 14, 14' and light sensors 15, 15' are positioned in a square configuration. Source 14 includes a lamp 16(La), a collimating lens 17, a beam splitter 18, and a window 19. Preferably the lamp provides a samll area light source located at the focus of lens 17 so as to produce a narrow collimated beam. The arrangement is designed to direct one narrow collimated beam of light 21 directly across the duct to light sensor 15, and another collimated beam 22 diagonally across the duct to sensor 15'. Advantageously the beam splitter 18 divides the light from source 16 into two equal parts, each of which will be denoted $I_a$. Source 14' is similar to 14, with the lamp denoted $L_b$. Diagonal paths 22, 22' make 45° angles with respect to the direct paths 21, 21'. Lamps 16 and 16' are supplied with energizing current from lamp supply 20.

In passing across the duct, light will be attenuated by an amount depending on the density of the smoke and the path length. This may be expressed in terms of optical transmittance T. The transmittance directly across the duct from source 14 to source 15 will be denoted $T_a$, corresponding to a path length $d_1$. This will also apply to light from 14' to 15' since the path lengths are equal. The diagonal paths have a length $d_2$. Over the portion of a diagonal path equal to $d_1$ the transmittance will be $T_a$. The transmittance of the remainder of the path, equal to $d_2 - d_1$, will be denoted $T_b$. The total transmittance along each diagonal path is the product of the individual transmittances and is $T_a T_b$.

Windows 19 and 19', in use, will acquire a covering of dirt, etc. which will reduce their transmittances. Further, different areas of the same window may acquire different dirt accumulations so that the transmittance for the direct and diagonal paths may be different. Accordingly the transmittances of windows 19, 19' will be denoted $t_{1a}$ and $t_{2a}$ for the direct paths 21, 21', and $t_{1b}$ and $t_{2b}$ for the diagonal paths 22, 22'. The windows at the sensors 15, 15' will be similarly subject to dirt accumulations, and their transmittances will be denoted $t_{1c}$ and $t_{2c}$ for the direct paths, and $t_{1d}$ and $t_{2d}$ for the diagonal paths.

Light sensors 15, 15' include photocells $P_1$ and $P_2$ onto which light is focussed by lenses 25, 25', thus producing a narrow reception beam angle at each photocell. Rotating segmented disks 26, 27 are driven by motors 28, 28' and have transparent (or open) and reflecting mirror sectors which alternately direct light beams from the direct and diagonal path to the photocells at the reception beam angles thereof. The disks will be further described below in connection with FIGS. 4a and 4b. The outputs of the photocells are amplified by amplifiers 29, 29'.

Assuming that the light from each source $L_a$ and $L_b$ is equally divided along direct and diagonal paths, the amount of light, say in lumens, from the sources will be dentoed $I_a$ and $I_b$ and the proportion directed along the two paths from respective sources will be denoted $k_a$ and $k_b$. The conversion constants of the sensors, say in converting lumens to volts, will be denoted $k_1$ and $k_2$. The output of sensor $P_1$ when receiving light from $L_a$ may then be written:

$$e_{1a} = k_a\, t_{1a}\, I_a\, T_a\, t_{1c}\, k_1 \qquad (1)$$

Similarly, the output of sensor $P_2$ when receiving light from the same source $L_a$ may be written:

$$e_{2a} = k_a\, t_{1b}\, I_a\, T_a\, T_b\, t_{2d}\, k_2 \qquad (2)$$

When sensore $P_1$ and $P_2$ receive light from source $L_b$, similar equations can be written as follows:

$$e_{1b} = k_b\, t_{2b}\, I_b\, T_a\, T_b\, t_{1d}\, k_1 \qquad (3)$$
$$e_{2b} 132\ k_b\, t_{2a}\, I_b\, T_a\, t_{2c}\, k_2 \qquad (4)$$

Dividing equation (2) by (1):

$$\frac{e_{2a}}{e_{1a}} = \left(\frac{t_{1b} t_{2d}}{t_{1a} t_{1c}}\right)\left(\frac{k_2}{k_1}\right) T_b \qquad (5)$$

Dividing equation (3) by (4):

$$\frac{e_{1b}}{e_{2b}} = \left(\frac{t_{2b} t_{1d}}{t_{2a} t_{2c}}\right)\left(\frac{k_1}{k_2}\right) T_b \qquad (6)$$

Equations (5) and (6) give the transmittance $T_b$ of aerosol-laden air or smoke in the conduit in terms of ratios of the sensor outputs, ratios of window transmittances, and ratios of the sensor conversion factors. Multiplying equations ( and (6) yields:

$$\frac{e_{2a}e_{1b}}{e_{1a}e_{2b}} = R_t T_b^2 \qquad (7)$$

where:

$$R_t = \frac{t_{1b}t_{2d}t_{2b}t_{1d}}{t_{1a}t_{1c}t_{2a}t_{2c}} \qquad (8)$$

Solving for $T_b$ gives:

$$T_b = \sqrt{\frac{c_{2a}e_{1a}}{e_{1a}e_{2b}}\left(\frac{1}{R_t}\right)} \qquad (9)$$

The numerator of the left term of equation (7), and the same term under the radical in equation (9), is the product of the photocell or sensor outputs corresponding to light transmitted over the longer paths $d_2$. The denominator is the product of the outputs corresponding to light transmitted over the shorter paths $d_1$. Hence the term is the quotient of the products of the sensor outputs corresponding to light trasmitted over the longer paths and over the shorter paths.

In equation (9), $R_t$ is a consolidation of the window transmittance factors and $T_b$ is the transmittance of the smoke over a predetermined path length which is $d_2 - d_1$ in FIG. 3. It will be noted that the illumination levels $I_a$ and $I_b$ of the light sources, the light proportionality constants $k_a$ and $k_b$, and the sensitivity factors $k_1$ and $k_2$ of the photocells have all been eliminated so that differences in these parameters at initial installation, and subsequent variations through aging, will have no effect on the determination of $T_b$.

If all the window transmittance factors were the same, both initially and after operation over a period of time, the quantity $R_t$ would be unity. However, this is not likely to be the case in practice. To analyze the effect, equation (8) may be re-grouped as follows:

$$R_t = \left(\frac{t_{1b}}{t_{1a}}\right)\left(\frac{t_{1d}}{t_{1c}}\right)\left(\frac{t_{2b}}{t_{2a}}\right)\left(\frac{t_{2d}}{t_{2c}}\right) \qquad (10)$$

By reference to FIG. 3, it will be seen that each of the bracketed terms is the ratio of the diagonal transmittance to the direct transmittance for a particular window. If each individual window retained its own ratio at unity (or at a fixed constant), the overall product $R_t$ would be unity (or a fixed constant) despite differences in the transmittances of different windows. This may occur in practice, particularly in a long straight conduit. If not, there are compensating facators as will be explained later.

The transmittance $T_b$ is that of distance $d_2 - d_l$ in FIG. 3. This can be expressed in terms of the transmittance $T_s$ of the exit stack diameter $d_s$ as follows:

$$T_s = T_b{}^c \qquad (11)$$

where:

$$c = \frac{d_s}{d_2 - d_1} \qquad (12)$$

It may be noted that although $d_2 - d_1$ is numerically less than the duct width, the measurement $T_b$ is the ratio of two transmittance measurements over at least the full duct width.

In order to measure the photocell output of equation (9), each of photocells $P_1$ and $P_2$ are alternately exposed to light from sources $L_a$ and $L_b$. This may be accomplished by the shutter disks 26 and 27, shown in more detail in FIGS. 4a and 4b. In these figures the numerals 1-4 indicate the time periods during which the corresponding sectors are in front of respective photocells. Each disk has two transparent or clear sectors denoted C, one fully reflective mirror sector denoted M, and one partially reflective mirror sector denoted $M_q$. The latter is used for continually checking the overal performance and may for example, be 50% reflecting.

During time period 1, photocell $P_1$ receives the direct beam from $L_a$, traveling along path 21. Hence its output is $e_{1a}$. In the same time period 1, photocell $P_2$ also receives light from $L_a$ traveling over the diagonal path 22 and reflected to it by the mirror sector M. The mirror blocks the direct beam. Accordingly its output is $e_{2a}$. Similarly, during time period 2 photocell $P_1$ receives light from $L_b$ along diagonal path 22' and the mirror sector M to yield $e_{1b}$ and photocell $P_2$ receives light from $L_b$ along direct path 21' to yield $e_{2b}$. These signals may then be multiplied and divided as set forth in equation (7). A suitable procedure is described later in connection with FIG. 7. Time periods 1 and 2 may be termed measuring periods.

Time periods 3 and 4 are used for self-testing purposes, and to give an alarm in case of malfunctioning. The transmittances or reflectivites of mirrors M will be denoted $T_q$ and are lower than those of mirror M, typically 0.5. During test periods these mirrors $M_q$ reduce the light transmitted to the corresponding sensor over the longer path length by a predetermined fraction of that transmitted during measuring periods.

During time period 3, a clear or open sector is in front of $P_1$ and a semi-reflecting mirror is in front of $p_2$. Hence equations (1) and (2) become:

$$e_{1(3)} = e_{1a} \qquad (13)$$

$$e_{2(3)} = T_q e_{2a} \qquad (14)$$

During time period 4, a semi-reflecting mirror is in front of $P_1$, and a clear segment is in front of $P_2$. Hence equations (3) and (4) become:

$$e_{1(4)} = T_q e_{1b} \qquad (15)$$

$$e_{2(4)} = e_{2b} \qquad (16)$$

As will be noted, the test signals corresponding to the clear sectors are substantially the same as the measuring signals, whereas those corresponding to the semi-reflecting mirror sectors are reduced.

The use of these signals for self-testing will be described in connection with FIG. 7. Inasmuch as they are produced in rapid succession following the measuring signals, both measuring and test signals are continually produced without interruption of service.

Figure 4A:
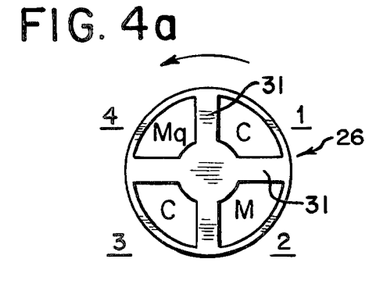
FIGS. 4a and 4b illustrate the rotating disks used in FIG. 3.
Figure 4B:
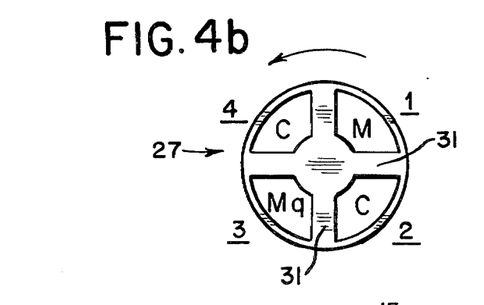

Shutter disks 26, 27 have opaque spoke 31 between adjacent segments to provide dark signals which may be used as described later.

Figure 5:
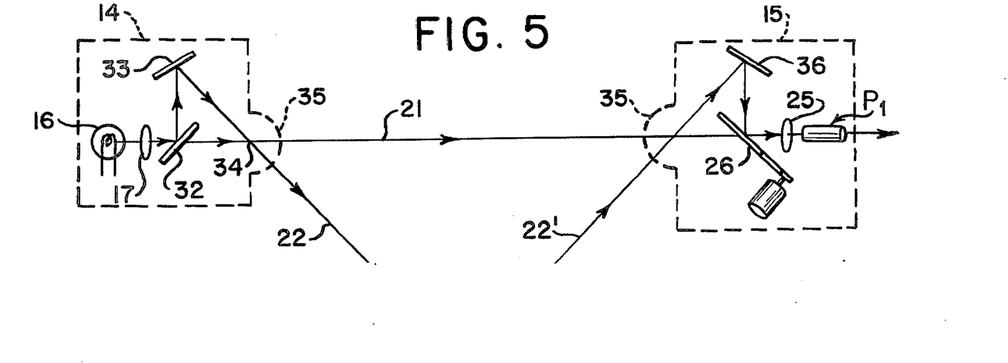
FIG. 5 illustrates a preferred arrangement of the light sources and light sensors of FIG. 3.

In the beam-splitters 18, 18' and at the shutter disks 26, 27 of FIG. 3, the incident and reflected rays make large angles with respect to the normals to their surfaces, 67.5° as shown. While satisfactory for explanatory purposes, superior designs are shown in FIG. 5. Here a beam splitter 32 is disposed at 45° with respect to the light path from lamp 16 and lens 17. One-half of the light continues through the beam splitter along path 21. The other half is reflected to mirror 33, which in turn reflects the light along path 22 passing through the center of curvature 34 of a spherically curved window 35. Thus the angles of incidence and reflection, with respect to the normal to the beam splitter surface, are considerably reduced. Similarly, at the receiving sensor 15, the plane of the rotating shutter disk 26 is at 45° to incident ray 21 which passes through the clear sectors to the lens 25 and photocell $P_1$. The diagonal ray 22' is reflected by stationary mirror 36 to impinge on mirror sectors of disk 26 at 45° to the normal thereof, and then reflected to $P_1$.

Figure 6A:
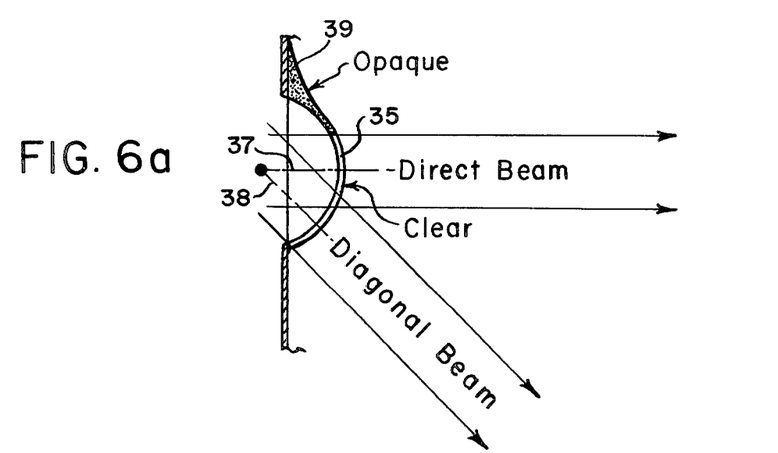
FIGS. 6a and 6b are views in perpendicular planes of a suitable window arrangement for the light sources and sensors.
Figure 6B:
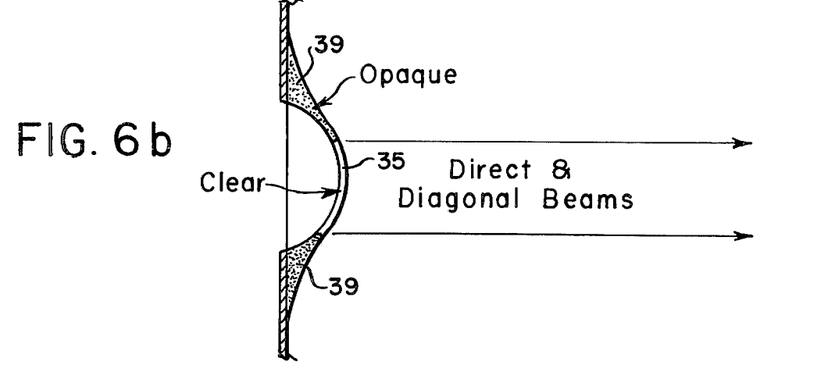

Considering now the effect of dirt accumulations on the windows 35, for a given window carrying a uniform coating of dirt the distances traversed through the window by direct and diagonal beams should be equal in order that their transmittance factors through the glass thickness and the dirt layer be matched. This is accomplished, as shown in FIG. 6a, by using a spherical surface for the window, with the axes of the collimated beams along respective radii 37, 38. With portions of the beams overlapping, the overlap area assists in assuring matched transmittance factors. In the plane perpendicular to that of FIG. 6a, as shown in FIG. 6b, opaque streamlined tapered cowls 39 may be provided to promote smooth flow of smoke past the window and thereby redue non-uniformity of dirt build-up, and also to shield the unused areas of the spherical surface.

Considering non-uniform dirt build-up, in a conduit it is possible for a greater build-up to occur on the upstream wide of a window. With the plane of the light sources and sensors at right angles to the smoke flow, as in FIG. 2a, it will be seen that any one-sided build-up will affect both upper and lower portions of the windows in like manner. Thus the window transmittances for both direct and diagonal beams will be similarly affected, and their ratio will be largely unchanged. Hence equation (10) remains approximately unity.

In the arrangement of FIG. 2b, and with reference to FIG. 3, it will be seen that if the upstream build-up is greaer than the downstream build-up, the ratio of diagonal to direct beam transmittances will decrease for the windows of light source 14 and sensor 15, and increase for light source 14' and sensor 15'. Hence the ratios change in compensating directions, and the overall value of equation (10) will remain at or near unity. In the arrangement of FIG. 2c a similar compensation occurs.

In a similar manner, any overall non-uniformity of dirt build-up due to gravity will be self-compensating.

The calculations for determining $T_b$ and $T_s$ in accordance with equations (9) and (11), and also for performing the self-checking calculations in accordance with equations (13– (16) may be made by analog or digital computers, as desired. Digital computation is preferred at the present time since it is less expensive and can yield any desired accuracy. FIG. 7 shows a suitable procedure predicated around the use of dedicated digital functional elements. Where the use of a programmable calculator or microprocessor is desired FIG. 7 can be the basis of an appropriate software program.

Figures 7, 7A:
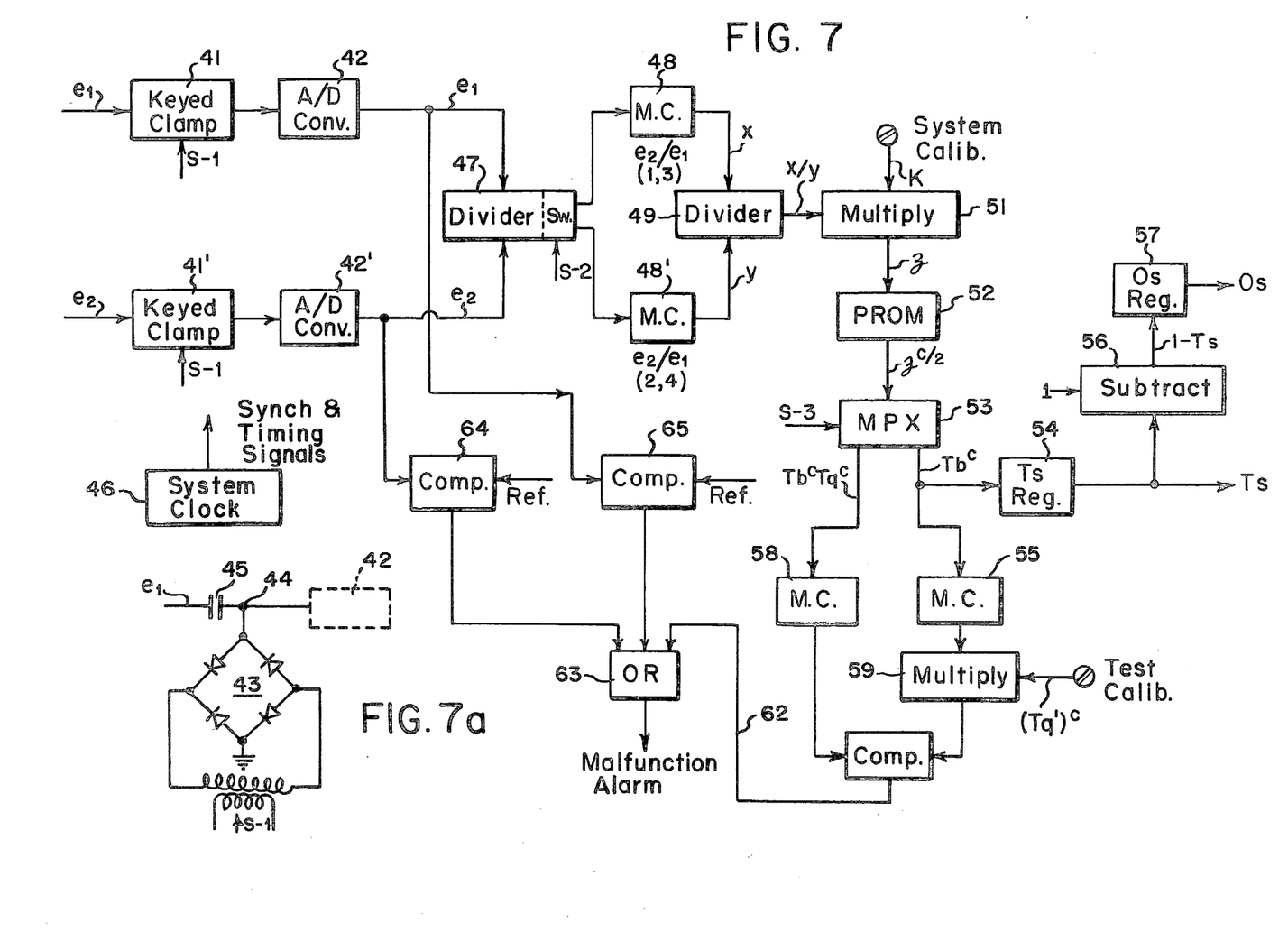
FIGS. 7 and 7a are diagrams of suitable computing arrangemsts for developing monitoring and self-test signals.

Referring to FIG. 7, amplified outputs $e_1$ and $e_2$ from sensors P-1 and P-2 of FIG. 3 are supplied through keyed clamps 41, 41' to respective analog-to-digital converters 42, 42'. As explained above, the accuracy of smoke determination is not affected by the sensitivity of the photocells. However, variations in the dark currents of the photocells will result in inaccuracies in the subsequent computations. Accordingly the keyed clamps bring the outputs of photocells $P_1$ and $P_2$ to the same reference level (e.g. ground) when no light is impinging thereon.

A suitable clamping cuircuit is shown in FIG. 7a. A pulsed synchronizing signal S-1 causes the diode bridge 43 to conduct when an opaque spoke 31 of te shutter disk 26, 27 (FIG. 4) is in front of the respective photocell, so as to ground point 44. This charges capacitor 45 to the dark current voltae of the photocell so that the voltage is effectively canceled and the output during the following sector of the disk always begins at the same reference level.

The synchronizing signal S-1 and other sysnchronizing and timing signals for the apparatus of FIG. 7 are produced by a system clock 46, in known manner. The motors 28, 28' for driving the disks are also in synchronism wiht clock 46.

The outputs $e_1$ and $e_2$ of converters 42, 42', now in digital form, are supplied to a first divider 47 which produces the quotient $e_2/e_1$. The output of the divider is alternately switched by sync signal S-2 to memory cells 48, 48'. Thus cell 48 receives signals during time periods 1 and 3, and cell 43' during time periods 2 and 4, as indicated. The memory cells are synchronized to provide outputs $X$ and $y$ to divider 49 at the proper times.

During measuring time period 1, cell 48 receives and stores the ratio $e_{2a}/e_{1a}$ in accordace with equation (5). During measuring time period 2, cell 48' preceives and stores the ratio $e_{2b}/e_{1b}$. At the end of time period 2 the resulting signals $x$ and $y$ are supplied to divider 49 which produces an output $x/y$. Accordingly the output will be the quotient of equation (7). It may be noted that in time period 2, divider 47 performs the inverse of equation (6), and therefore the subsequent operation is a division rather than a mulitiplication. Either procedure may be followed, as desired.

The output of divider 49 is mulitplied in 51 by a system calibration constant K which takes into account values of $R_t$ other than unity, and other factors as will be described hereinafter.

The output of multiplier 51 is designated z. For measuring time periods 1 and 2, $z$ will be $T_b^2$ as used in equation (7). The square root is then taken to obtain $T_b$, and the latter is raised to the power c in order to obtain the stack exit diameter transmittance $T_s$ of equation (11). This is conveniently accomplished by a programmable read-only memory designated PROM 52. The resultant is supplied by multiplexer 53 to the $T_s$ register 54 and to memory cell 55 at the end of time period 2, under the control of sync signals S-3.

If opacity rather than transmittance is desired, the quantity $T_s$ is subtracted from unity in 56 and supplied to the $O_s$ register 57. Registers 54 and 57 may be designed to provide suitable outputs for indicating, recording, remote data link transmission, etc.

During test time periods 3 and 4, the apparatus is in its self-checking mode of operation wherein the semi-reflecting mirrors $M_q$ are in operation. Using equations (13) – (16) the output of divider 49 becomes:

$$R_t T_q^2 T_b^2 \qquad (16)$$

This is processed in multiplier 51 and PROM 52 in the same manner as described above, and the resultant $T_b^c T_q^c$ is supplied by multiplexer 53 to memory cell 58 at the end of time period 4. In orer to permit convenient comparison, the output of memory cell 55 is multiplied in 59 by the quantity $(T_q')^c$, where $T_q'$ is the normal value of the transmittance of semi-mirrors $M_q$. The outputs of memory cell 58 and multiplier 59 are then fed to a comparator 61.

If the apparatus is performing properly, both inputs to comparator 61 will be equal. In the event of a malfunction, it is highly probable that the equality will be disrupted, thus supplying an error signal through line 62 to OR 63 which sounds off an alarm. Suitable limits may be employed so that small error signals will not actuate the alarm.

It will be understood that the multiplication in 59 can also be considered to be a division, since multiplication by a factor of, say, 0.5 is equivalent to dividing by a factor of 2. Compensating factors may be introduced in the outputs of either 55 or 58, or both, to yield resultants which can be readily compared. Or, other means may be provided for comparing the quotients from divider 49 produced during measuring and test periods.

A further check is provided by feeding the outputs $e_1$ and $e_2$ to respective comparators 64, 65, along with reference signals. Although the system is insensitive to variations in most of the optical parameters, it is possible that deterioration in lamp brightness and photocell sensitivity, or excessive dirt build-up, could result in such low electrical signal outputs as to fall below the operating range of the A/D converters 42, 42', or otherwise be too low for satisfactory results. The reference levels of the comparators 64, 65 may be selected so that the outputs to OR63 will sound an alarm if $e_1$ or $e_2$ is below a satisfactory level.

Considering now the value K which is supplied to multiplier 51 for system calibration, this is to remove fixed errors which may be introduced by manufacturing tolerances, etc. in parts of the optical system. Part of the error may be a departure from unity in the quantity $R_t$ of equation (7). In addition, the beam splitters 18, 18' may not divide the beam precisely equally, and the reflectivity of the mirror sectors M may not be 100%. These additional factors may be taken into account by assuming that the direct portions from beam splitters 18, 18' are $s_1$ and $s_2$, respectively. The the reflected portions will be $(1-s_1)$ and $(1-s_2)$. Also assume that the mirror segments M of disks 26 and 27 have reflectivity factors $r_1$ and $r_2$. These added factors may be introduced into equations (1) – (4) for the light paths involved. By then proceeding as in the case of equations (5) – (7), the following relationship can be obtained:

$$\frac{e_{2a} e_{1b}}{e_{1a} e_{2b}} = \frac{R_t T_b^2}{K} \qquad (17)$$

where $$\frac{1}{K} = \frac{(1-s_1)(1-s_2) r_1 r_2}{s_1 s_2} \qquad (18)$$

Accordingly, by multiplying the output of divider 49 by K in multiplier 51, the factor 1/K is eliminated.

In practice, the system may be calibrated by applying an adjustable multiplying factor to 51. Then, when the conduit is optically clear of any particulate matter, the factor may be set at a point where the output indication of transmittance $T_s$ reads unity (or opacity $O_s$ reads zero). Such an adjustment will also take care of any departures of $R_t$ from unity.

It will be understood that additional timing and strobe signals may be used to yield the operation described for FIG. 7. In the event a programmable calculator or microprocessor is employed, such timing signals as is required will also be dependent upon the detailed make-up of the software program.

The output of multiplier 51 during time periods 1 and 2 is $T_b^2$, as used in equation (7). The programmable read-only memory PROM 52 provides a function shaping operation which raises $T_b^2$ to the $c/2$ power, where c is as defined in equation (12), so as to compute $T_s$, as is defined in equations (11). By re-programming PROM 52, different values of c may be accommodated to take care of differing duct and stack installation dimensions. In a broader sense, distances other than $d_s$, the exit stack diameter, may also be selected and the appropriate calculation made of both transmittance and opacity.

It will be understood that transmittance and opacity are alternative ways of expressing te light-attenuating property of the particulate matter in the gaseous medium, and that optical density is a further way of expressing either quantity. Optical density D, transmittance T, and opacity O are related to each other by the fundamental relationship:

$$D = \log_{10} \frac{1}{T} = \log_{10} \frac{1}{(1-O)} \qquad (19)$$

Apparatus as above described is satisfactory for operation in a relatively light-tight environment. Where there is a minor amount of extraneous light leakage into the duct, the narrow acceptance angle of he sensor optics will tend to minimize errors from this source.

In the event the ambient light level is excessively high, its effect can be nullified by a modification of the basic apparatus. This modification consists of pulsing both light sources 16 and 16' simultaneously by driving lamp supple 20 from a common signal source derived from the system clock 46 (FIG. 7). The pulse rate is relatively high compared to the rotational speed of disks 26 and 27 so that each sensor receives light in turn from $L_a$ and $L_b$ in the form of square wave pulse bursts. The previously described clamp circuit 43 is provided with synchronizing signal pulses which are synchronized with the pulsing of te light sources so that, during each of the short time intervals that the light sources $L_a$ and $L_b$ are extinguished, the diode bridge 43 conducts so as to ground point 44. This charges capacitor 45 to the sum of both the ambient light signal and the photocell dark current. The capacitor voltage thus comprises a cancellation signal which is subtracted from the composite photocell signal during the time intervals the light sources are pulsed on.

As a further refinement, the light sources $L_a$ and $L_b$ can be supplied with separate bursts of square wave pulses on an alternating basis. This is possible since, in the operation of the apparatus, both photosensors first receive light from one source and then from the other source.

In the specific embodiment of FIG. 3, the reduction in light to sensors P-1 and P-2 during the test periods is by semireflecting mirrors on the rotating disks 26, 27 and light transmitted to the sensors over the longer paths 22, 22' is reduced. Instead of reducing light from the longer paths, it is possible to reduce the light transmitted to the sensors over the shorter paths 21, 21'. This may be accomplished by using calibrated density filters, say of 50% transparency, in the direct paths during the test periods. For example, the clear sector 3 of disk 26 and the clear sector 4 of disk 27 may be selected to give a transmittance $T_q$ which is a fraction, say 50%, of the clear sectors which operate during the measuring periods. Then mirror sectors $M_q$ may have the same reflectivity as mirror sectors M. In such case the expression (16) would become:

$$\frac{R_t T_b^2}{T_q^2} \quad (20)$$

In FIG. 7 the multiplying factor to multiplier 59 can be changed accordingly, or the output of memory cell 58 multiplied by an appropriate factor so that both inputs to comparator 61 are equal if the apparatus is performing properly.

It is also possible to dispense with the mechanically rotating disks and replace them by stationary beam splitters similar to those in the light sources. The light sources may then be actuated in alternating sequence. Thus each photosensor receives light in alternating sequence from directly across the duct (short path) and over the diagonal path (long path). If improved ambient light cancellation is required, each light source can be activated by separate bursts of square wave pulses. The clamp circuit 43 would then be driven by a switching signal which is synchronized with the individual pulses of the square wave bursts as described above. Other means would need to be employed if the test features of the invention are to be retained.

Although the square configuration of FIG. 3 is optically advantageous, other configurations are possible. Thus in FIG. 8a the spacing between light sources A and B and between light sensors C and D is greater than the distance directly across the conduit. This makes the diagonal path lengths A-14 D, B-C much greater than the direct path lengths A-C, B-D, which may be advantageous per se. However, the greater angles between the diagonal and direct paths increase the problem of optical design, and the problem due to dirt accumulation may be more severe.

Figure 8A:
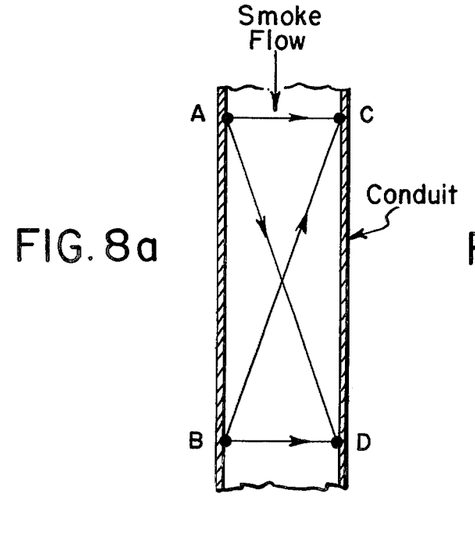
FIGS. 8a and 8b illustrate alternative arrangements of light sources and light sensors.
Figure 8B:
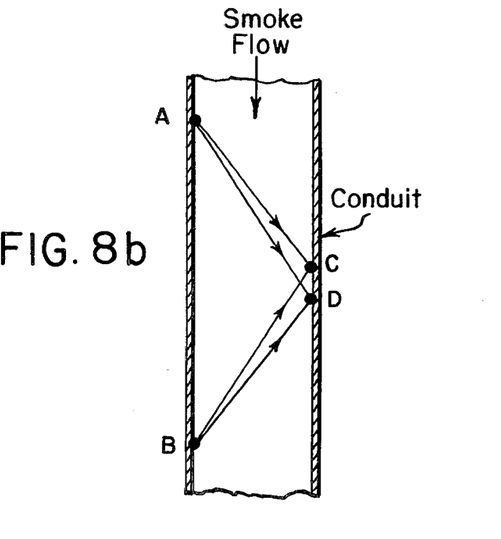

FIG. 8b is another possible configuration. Here the small angles CAD and CBD favor optical design and uniform dirt accumulation, but the large angles ACB and ADB are less favorable.

In both FIGS. 8a and 8b, A and B may be light sources and C and D light sensors, or vice versa.

The invention has been described in connection with specific embodiments thereof. It will be understood that modifications may be made therein, and selected features employed and others omitted, as meets the requirements of a particular application or the views of the designer.

I claim;

1. Apparatus for measuring the transmittance or opacity of a gaseous medium carrying particulate matter through a conduit which comprises
    a. spaced first and second light sources and spaced first and second light sensors positioned on opposite walls of said conduit with equal shorter path lengths between first source and first sensor and between second source and second sensor and equal longer path lengths between first source and second sensor and between second source and first sensor,
    b. means at each light source for producing and directing narrow collimated beams toward each light sensor,
    c. means at each light sensor for producing a narrow reception beam angle,
    d. means for exposing each sensor to collimated beams from said sources alternately during measuring periods and directing the collimated beams to the sensor at said reception beam angle thereof,
    e. and computing means for utilizing the outputs of said sensors to produce the quotient of the products of the outputs corresponding to light transmitted over said longer paths and over said shorter paths and producing from the quotient an output corresponding to the transmittance or opacity over a predetermined distance of said gaseous medium carrying particulate matter.

2. Apparatus according to claim 1 including test means adjacent each sensor for reducing the light transmitted to the sensor over one of said paths by a predetermined fraction during test periods alternating with said measuring periods, said computing means producing a said quotient from the sensor outputs produced during said test periods, and test means for producing test signal outputs from the quotients corresponding to the measuring and test periods.

3. Apparatus according to claim 1 including windows in said walls of the conduit adjacent said sources and sensors respectively, said means for producing and directing narrow collimated beams at the sources and for producing narrow reception beam angles at the sensors being positioned between the windows and the sources and sensors, respectively.

4. Apparatus according to claim 3 in which the means for producing and directing narrow collimated beams at the sources include beam splitting means.

5. Apparatus according to claim 4 in which the means for exposing each sensor to beams from said sources alternately includes a rotating disk having transparent and mirror sectors for directing beams to the sensor transmitted over said shorter and longer paths, respectively.

6. Apparatus according to claim 5 in which said disk has opaque spokes between the sectors thereof, and including clamping means for clamping the outputs of said sensors corresponding to said opaque spokes to a predetermined reference level.

7. Apparatus according to claim 5 in which said rotating disk includes a mirror sector of high reflectivity and a mirror sector of lower reflectivity, said sectors of high and lower reflectivity operating during respective measuring and test periods, said computing means producing a said quotient from the sensor outputs produced during said test periods, and test means for producing test signal outputs from the quotients corresponding to the measuring and test periods.

8. Apparatus according to claim 7 in which said test means includes means for producing test signal components from the quotients corresponding to the measuring and test periods, means for multiplying one of said components by a factor compensating for the difference in reflectivity of said high and lower reflectivity mirrors, and means for comparing the compensated component with the other of said components to yield a test signal output.

9. Apparatus according to claim 1 in which said sensors simultaneously receive light from one source transmitted over respectively shorter and longer path lengths and alternately receive light from the other source transmitted over respectively longer and shorter path lengths, and said computing means includes means for producing ratios of the sensor outputs corresponding to light transmitted thereto over said shorter and longer path lengths and vice versa, and means for producing from said ratios the said quotient.

10. Apparatus according to claim 1 including comparator means for comparing the output output of a said sensor with a predetermined reference to produce an alarm signal when the output of the sensor is less than said predetermined reference.

11. Apparatus according to claim 1 in which said sources and sensors are positioned positioned a plane perpendicular to the path of travel of said gaseous medium medium the conduit.

12. Apparatus according to claim 1 in which said sources and sensors are positioned in a plane parallel to the path of travel of said gaseous medium in the conduit.

13. Apparatus according to claim 3 in which the portions of said windows through which said collimated beams pass are spherically curved.

14. Apparatus according to claim 13 in which said windows are flared into said walls in the direction of the flow of said gaseous medium thereby.

15. Apparatus according to claim 1 in which said sources and sensors are positioned in a plane with the first and second sensors directly across said conduit from said first and second sources respectively, and the second and first sensors diagonally across the conduit from the first and second sources respectively, the diagonal light paths between sources and sensors making angles of approximately 45° with respect to the direct light paths therebetween.

16. Apparatus according to claim 15 including windows in the walls of said conduit adjacent said sources and sensors respectively, said means at each source for producing and directing narrow collimated beams toward each sensor including collimating and beam splitting means between each source and the respective window, and said means for producing a narrow reception beam angle at each sensor and exposing the sensor to beams from the sources alternately includes a rotating disk and collimating means between the respective window and sensor, said disk having transparent and mirror sectors for directing light from respective direct and diagonal paths alternately to the respective sensor.

17. Apparatus according to claim 16 in which said rotating disk includes a mirror sector of high reflectivity and a mirror sector of lower reflectivity, said sectors of high and lower reflectivity operating during respective measuring and test periods, said computing means producing a said quotient from the sensor outputs produced during said test periods, and test means for producing test signal outputs from the quotients corresponding to the measuring and test periods.

18. Apparatus according to claim 17 in which the portions of said windows through which said collimated beams pass are spherically curved, said collimating and beam splitting means at each source are designed and adapted for directing beams through the corresponding window to each sensor with their center lines approximately along radii of the window, and said rotating disk and collimating means at each sensor are designed and adapted for receiving beams which pass through the respective window with their center lines approximately along radii of the window and directing the beams to the sensor.

19. Apparatus according to claim 1 including means for actuating said light sources on and off during said measuring periods, and clamping means for clamping the outputs of said sensors to a predetermined reference level during off intervals of said light sources.

* * * * *

UNITED STATES PATENT AND TRADEMARK OFFICE
CERTIFICATE OF CORRECTION

PATENT NO. : 4,017,193
DATED : April 12, 1977
INVENTOR(S) : Leo Loiterman

It is certified that error appears in the above-identified patent and that said Letters Patent are hereby corrected as shown below:

Column 1, line 11, "for" should be --from--
          line 14, "frequaent" should be --frequent--
          line 24, "ccompliance" should be --compliance--
          line 49, "smoks" should be --smoke--
          line 66, "beam" should be --beams--

Column 2, line 12, "output" should be --outputs--
          line 20, "paht" should be --path--
          line 25, "ro" should be --or--
          line 44, "periiods" should be --periods--
          line 54, "ae" should be --are--
          line 57, "thesen-" should be --the sen- --

Column 3, line 19, "arrangemsts" should be --arrangements--
          line 26, "Reffering" should be --Referring--

Column 4, line 34, "dentoed" should be --denoted--
          line 47, "sensore" should be --sensors--
          line 51, "$e_{2b}132$" should be --$e_{2b}=$ --

Column 5, line 2, "(and" should be --(5) and--
          line 18, "$T_b = \sqrt{c_{2a} e_{1a}}$" should be --$T_b = \sqrt{e_{2a} e_{1b}}$ --

Column 6, line 9, "output" should be --outputs--
          line 38, "M" should be --$M_q$--
          line 46, "p_2" should be --$P_2$--

Column 7, line 1, "spoke" should be --spokes--
          line 27, "by direct" should be --by the direct--
          line 37, "mote smooth" should be --mote a smooth--
          line 38, "redue" should be --reduce--
          line 53, "greaer" should be --greater--

UNITED STATES PATENT AND TRADEMARK OFFICE
CERTIFICATE OF CORRECTION

PATENT NO. : 4,017,193
DATED : April 12, 1977
INVENTOR(S) : Leo Loiterman

It is certified that error appears in the above-identified patent and that said Letters Patent are hereby corrected as shown below:

Column 8, line 17, "cuircuit" should be --circuit--
line 19, "of te" should be --of the--
line 22, "voltae" should be --voltage--
line 31, "wiht" should be --with--
line 39, "X" should be --x--
line 42, "accordace" should be --accordance--
line 43, "preceives" should be --receives--
line 57, "Z" should be --Z-- (in italics)

Column 9, line 13, "orer" should be --order--
line 15, "$T_q'$." should be --$T_q'$--

Column 10, line 27, "equations" should be --equation--
line 32, "calculation" should be --calculations--
line 35, "te" should be --the--
line 49, "he" should be --the--
line 55, "supple" should be --supply--
line 62, "te" should be --the--

Column 11, line 54, "A-14D," should be --A-D,--

UNITED STATES PATENT OFFICE
CERTIFICATE OF CORRECTION

Patent No. 4,017,193          Dated April 12, 1977

Inventor(s) Leo Loiterman

It is certified that error appears in the above-identified patent and that said Letters Patent are hereby corrected as shown below:

Column 13, line 24, "output output" should read --output--.
          line 29, "positioned positioned" should read --positioned--.
          line 31, "medium medium" should read --medium--.

This certificate supersedes certificate issued September 27, 1977

Signed and Sealed this

Second Day of May 1978

[SEAL]

Attest:

RUTH C. MASON
Attesting Officer

LUTRELLE F. PARKER
Acting Commissioner of Patents and Trademarks